United States Patent
Choi et al.

(10) Patent No.: US 9,532,637 B2
(45) Date of Patent: Jan. 3, 2017

(54) COSMETIC COMPOSITION CARRIER COMPRISING URETHANE FOAM

(71) Applicant: AMOREPACIFIC CORPORATION, Seoul (KR)

(72) Inventors: Jung Sun Choi, Yongin-si (KR); Kyung Nam Kim, Yongin-si (KR); Ha Jin Jung, Yongin-si (KR); Kyung Ho Choi, Yongin-si (KR); Yeong Jin Choi, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 143 days.

(21) Appl. No.: 14/391,538

(22) PCT Filed: Apr. 12, 2013

(86) PCT No.: PCT/KR2013/003105
§ 371 (c)(1),
(2) Date: Oct. 9, 2014

(87) PCT Pub. No.: WO2013/154395
PCT Pub. Date: Oct. 17, 2013

(65) Prior Publication Data
US 2015/0104235 A1    Apr. 16, 2015

(30) Foreign Application Priority Data

Apr. 13, 2012 (KR) .......... 10-2012-0038628

(51) Int. Cl.
| A45D 40/26 | (2006.01) |
| A61Q 17/04 | (2006.01) |
| A61K 8/87 | (2006.01) |
| A45D 34/04 | (2006.01) |
| A61Q 1/10 | (2006.01) |

(52) U.S. Cl.
CPC .............. *A45D 40/26* (2013.01); *A45D 34/04* (2013.01); *A61K 8/87* (2013.01); *A61Q 17/04* (2013.01); *A45D 2200/1009* (2013.01); *A45D 2200/1018* (2013.01); *A45D 2200/1036* (2013.01); *A61K 2800/87* (2013.01); *A61Q 1/10* (2013.01)

(58) Field of Classification Search
CPC combination set(s) only.
See application file for complete search history.

(56) References Cited

U.S. PATENT DOCUMENTS

| 6,342,237 B1 | 1/2002 | Bara |
| 6,391,233 B1 * | 5/2002 | Otani ................... B29C 67/202 264/344 |
| 8,580,863 B2 * | 11/2013 | Shibaya ............. A41D 31/0044 521/154 |
| 2007/0253914 A1 | 11/2007 | Ha et al. |
| 2011/0014254 A1 | 1/2011 | Choi et al. |

FOREIGN PATENT DOCUMENTS

| CN | 1284322 | 2/2001 |
| JP | 2003012457 A | 1/2003 |
| JP | 2003093152 A | 4/2003 |
| JP | 2007330771 A | 12/2007 |
| JP | 2008264060 A | 11/2008 |
| KR | 1020090100643 A | 9/2009 |
| WO | 2012128589 | 9/2012 |

OTHER PUBLICATIONS

Chinese Office Action-Chinese Application No. 201380031634.7 dated Dec. 21, 2015.
Wu Shimin et al., "Concise and Fine Chemical engineering Dictionary, The first edition", Liaoning Science and Technology Publishing Company, Jun. 1999, pp. 930.
European Search Report-EP Application No. 13776292.8 dated Nov. 3, 2015.
International Search Report for International Application No. PCT/KR2013/003105 dated Jul. 3, 2013.
Written Opinion for International Application No. PCT/KR2013/003105 dated Jul. 3, 2013.
Taiwanese Office Action—Taiwanese Application No. 102113198 dated Aug. 26, 2016, citing CN1284322.

* cited by examiner

*Primary Examiner* — David Walczak
(74) *Attorney, Agent, or Firm* — Cantor Colburn LLP

(57) ABSTRACT

A cosmetic includes a cosmetic composition of viscosity of 1,000-5,000 centipoise (cps) or 15,000-60,000 cps; and a urethane foam carrier, which is impregnated with the cosmetic composition. The urethane foam has a hardness of 50 to 100 when measured with an Asker hardness tester type F before impregnation and a number of pores per inch (ppi) of greater than or equal to 10 but less than 90 when the cosmetic composition has a viscosity of 1,000-5,000 centipoise (cps). The urethane foam has a hardness of greater than or equal to 1 but less than 50 when measured with an Asker hardness tester type F before impregnation and a number of pores per inch (ppi) of 90 to 200 when the cosmetic composition has a viscosity of 15,000-60,000 cps.

6 Claims, No Drawings

COSMETIC COMPOSITION CARRIER COMPRISING URETHANE FOAM

TECHNICAL FIELD

The present disclosure relates to a carrier for a cosmetic composition comprising a urethane foam.

BACKGROUND ART

Although a cosmetic composition was mainly used indoors in the past, it is frequently used outdoors with the change in lifestyles, comprising increased leisure activities. Accordingly, the need of a cosmetic composition which is convenient in use and carrying is increasing.

Although a cosmetic which is convenient to use and carry was developed by impregnating a cosmetic composition in a urethane foam, the urethane foam commonly used as a carrier for a cosmetic composition is applicable only to emulsion-type cosmetic compositions having viscosity of about 5,000-15,000 cps. With the recent trend toward naturally-looking makeup, there is a high preference for low-viscosity cosmetic compositions that allow lightly-looking makeup. There is also a consistent demand on a high-viscosity cosmetic composition capable of providing superior covering and moisturizing effect. Accordingly, there is a need for a carrier for a cosmetic composition that can stably hold low-viscosity and high-viscosity cosmetic compositions and allows convenient use and carry of cosmetics.

DISCLOSURE

Technical Problem

The present disclosure is directed to providing a carrier for a cosmetic composition capable of easily impregnating cosmetic compositions of various viscosities.

The present disclosure is also directed to providing a cosmetic comprising the carrier for a cosmetic composition, which is convenient to use and carry.

Technical Solution

In one general aspect, the present disclosure provides a carrier for a cosmetic composition comprising a urethane foam having a hardness of 1-100 when measured with an Asker hardness tester type F before impregnation, wherein the cosmetic composition has a viscosity of 1,000-5,000 centipoise (cps) or 15,000-60,000 cps.

In another general aspect, the present disclosure provides a cosmetic comprising the carrier for a cosmetic composition which comprises a cosmetic composition.

Advantageous Effects

Since a carrier for a cosmetic composition according to the present disclosure, which comprises a urethane foam whose hardness and number of pores per inch are controlled according to the viscosity of the cosmetic composition, is capable of impregnating cosmetic compositions of various viscosities comprising low-viscosity and high-viscosity cosmetic compositions, which are generally known to be difficult to be impregnated in a urethane foam, it can provide improved stability, feeling of use and portability of cosmetics. Accordingly, cosmetics satisfying various needs of users can be provided.

BEST MODE

As used herein, a "carrier" refers to a material capable of impregnating any substance or component which may be a composition. It can also be expressed as a "medium". As used herein, "impregnating ability" refers to the ability to impregnate and hold any substance or component.

As used herein, a "urethane foam" refers to polyurethane which has been foamed and then solidified and may also be referred to as a "foamed urethane".

In an aspect, the present disclosure provides a carrier for a cosmetic composition comprising a urethane foam having a hardness of 1-100 when measured with an Asker hardness tester type F before impregnation, wherein the cosmetic composition has a viscosity of 1,000-5,000 centipoise (cps) or 15,000-60,000 cps. The carrier for a cosmetic composition, which comprises a urethane foam with one or more of hardness and number of pores per inch (ppi) controlled according to the viscosity of the cosmetic composition, is capable of stably impregnating the cosmetic composition and allows convenient use and carrying of the cosmetic composition.

In an exemplary embodiment of the present disclosure, the viscosity may be measured using a viscometer, for example, LVDV II+PRO or RVDV III ULTRA, spindle No. 63 or spindle No. 64, at 5 rpm or 12 rpm, but is not limited thereto.

In an exemplary embodiment of the present disclosure, if the cosmetic composition has a low viscosity, specifically if the cosmetic composition has a viscosity of 1,000-5,000 cps, more specifically 1,500-4,000 cps, further more specifically 2,000-3,000 cps, a urethane foam having a hardness measured with an Asker hardness tester type F of 50-100, specifically 60-90, more specifically 70-80, may be used as a carrier. If the urethane foam has a hardness below 50, the low-viscosity cosmetic composition cannot be stably impregnated and separation or precipitation of the cosmetic composition may occur. And, if the urethane foam has a hardness exceeding 100, the low-viscosity cosmetic composition may not be easily ejected.

In another exemplary embodiment of the present disclosure, if the cosmetic composition has a low viscosity as described above, a urethane foam having a number of pores per inch of greater than or equal to 10 but less than 90, specifically 20-80 ppi, more specifically 30-70 ppi, may be used as a carrier. If the number of pores per inch is smaller than 10 ppi, it may be difficult to control the fluidity of the low-viscosity cosmetic composition and to impregnate an adequate amount of the low-viscosity cosmetic composition. And, if the number of pores per inch of the urethane foam exceeds 90 ppi, the low-viscosity cosmetic composition may not be effectively impregnated and separation or precipitation of the cosmetic composition may occur. In the present disclosure, the "number of pores" means the number of pores per inch of the urethane foam. The number of pores may mean an average number of pores per inch of a horizontal or vertical line measured according to WI-QA-14 (ASTM).

In an exemplary embodiment of the present disclosure, if the cosmetic composition has a high viscosity, specifically if the cosmetic composition has a viscosity of 15,000-60,000 cps, more specifically 20,000-55,000 cps, further more specifically 30,000-50,000 cps, a urethane foam having a hardness measured with an Asker hardness tester type F of greater than or equal to 1 but less than 50, specifically greater than or equal to 5 but less than 45, more specifically greater than or equal to 10 but less than 40, more specifically 15-35, may be used as a carrier. If the urethane foam has a hardness below 1, the high-viscosity cosmetic composition may be ejected excessively. And, if the urethane foam has a hardness of 50 and over, the high-viscosity cosmetic composition may not be uniformly impregnated in the urethane foam.

In another exemplary embodiment of the present disclosure, if the cosmetic composition has a high viscosity as described above, a urethane foam having a number of pores per inch of 90-200 ppi, specifically 100-190 ppi, more specifically 110-180 ppi, more specifically 120-170 ppi, may be used as a carrier. If the number of pores per inch is smaller than 90 ppi, the high-viscosity cosmetic composition may not be uniformly impregnated in the urethane foam. And, if the number of pores per inch of the urethane foam exceeds 200 ppi, the urethane foam may have unsatisfactory durability and may deteriorate the feeling of use of the cosmetic composition.

In an exemplary embodiment of the present disclosure, the urethane foam may be a polyester-based urethane foam or a polyether-based urethane foam. The polyether-based urethane foam has a larger pore size than the polyester-based urethane foam and exhibits higher air permeability and better cushioniness, softness, flexibility and elasticity.

In an exemplary embodiment of the present disclosure, the urethane foam may have a reticulated structure having fine pores. The reticulated structure may be advantageous in uniformly impregnating the cosmetic composition with higher efficiency. As used herein, the "pore" of the urethane foam may mean the pore of a urethane foam having a reticulated structure.

In an exemplary embodiment of the present disclosure, the urethane foam may have an open-cell structure. If the urethane foam has a closed-cell structure, the cosmetic composition may not be easily absorbed since an air bubble is captured in the urethane foam. In the present disclosure, the open-cell structure refers to a net-like structure and the closed-cell structure refers to a balloon-like structure having a foamed film through which air or water cannot pass easily.

In an exemplary embodiment of the present disclosure, the cosmetic composition may be an aqueous dispersion, an oily dispersion, a water-in-oil (W/O) emulsion or an oil-in-water (O/W) emulsion. The cosmetic composition that can be used for a carrier for a cosmetic composition according to another exemplary embodiment of the present disclosure may not substantially contain an emulsifying agent which deteriorates feeling of use.

In an exemplary embodiment of the present disclosure, the cosmetic composition may be any cosmetic composition for skin care or makeup. Specifically, the cosmetic composition may be formulated as makeup primer, makeup base, foundation, powder, twin cake, lipstick, lip gloss, eye shadow, eyebrow, concealer, lip liner, blusher, sunscreen, lotion, cream or essence, more specifically makeup primer, makeup base, liquid or solid foundation, powder, twin cake, lipstick, lip gloss, eye shadow, eyebrow, concealer or blusher, but is not limited thereto. In another exemplary embodiment of the present disclosure, if the cosmetic composition is a sunscreen, the carrier for a cosmetic composition according to the present disclosure improves stability and portability of a cosmetic regardless of the viscosity of the sunscreen. In addition, since hand washing is unnecessary after application of the sunscreen to the skin by ejecting from the carrier, the user can conveniently enjoy anti-UV effect outdoors.

In another aspect, the present disclosure provides a cosmetic comprising the carrier for a cosmetic composition which contains a cosmetic composition. The cosmetic, which comprises the carrier for a cosmetic composition according to the present disclosure, can uniformly impregnate low-viscosity and high-viscosity cosmetic compositions for a long time, allows ejection of an adequate amount of the cosmetic composition and exhibits excellent long-term durability. A cosmetic composition according to another embodiment of the present disclosure may be provided in a container which comprises a lower portion for accommodating the cosmetic and an upper portion having a cover and, optionally, a mirror, which is usually called a compact. If the cosmetic comprising the carrier for a cosmetic composition containing a sunscreen is provided as a compact, use and carrying are more convenient as compared to the existing sunscreen cosmetic and a cooling effect may also be provided.

Hereinafter, the present disclosure will be described in detail through examples, comparative examples and test examples. However, the following examples, comparative examples and test examples are for illustrative purposes only and it will be apparent to those of ordinary skill in the art that the scope of the present disclosure is not limited by the examples.

Preparation Examples 1-3

Preparation of Cosmetic Compositions

Cosmetic compositions having viscosities of 1,000-5,000 cps, greater than 5,000 but less than 15,000 cps and greater than or equal to 15,000 but less than 60,000 cps were prepared as described in Table 1.

Specifically, anti-UV agents were dissolved by adding to oily components. After emulsification and mixing with surfactants, the mixture was homogenized by stirring at 80° C. After mixing with pigments, the mixture was homogenized by stirring again to prepare an oily mixture. In a separate mixer, aqueous components were mixed and completely dissolved by stirring at 80° C. to prepare an aqueous component mixture. The aqueous mixture was slowly added to the oily mixture prepared above and emulsified using a homogenizing mixer. After cooling to 50° C. and adding skin-protecting components (humectants), fragrance, etc., the mixture was cooled to obtain a cosmetic composition.

TABLE 1

| | | Components (wt %) | Preparation Example 1 | Comparative Preparation Example 2 | Preparation Example 3 |
|---|---|---|---|---|---|
| Oily mixture | Oily components | Ozokerite | — | 0.2 | 1.0 |
| | | Dicaprylyl carbonate | 10.00 | 10.00 | 10.00 |
| | Preservative | Methylparaben | 0.100 | 0.100 | 0.100 |
| | Anti-UV agents | Octyl methoxycinnamate | 7.000 | 7.000 | 7.000 |
| | | Isoamyl p-methoxycinnamate | 2.000 | 2.000 | 2.000 |

TABLE 1-continued

| | Components (wt %) | | Preparation Example 1 | Comparative Preparation Example 2 | Preparation Example 3 |
|---|---|---|---|---|---|
| | Pigment | Disteardimonium hectorite | 0.2 | 1.50 | 2.00 |
| | Oily component | Decamethylcyclopentasiloxane | 16.00 | 16.00 | 16.00 |
| | Surfactants | Sorbitan sesquioleate | 2.000 | 2.000 | 2.000 |
| | | Lauryl PEG/PPG-18/18 methicone | 1.500 | 1.500 | 1.500 |
| | Pigments | Poly(methyl methacrylate) | 5.00 | 5.00 | 5.00 |
| | | Titanium dioxide/aluminum hydroxide/stearic acid | 7.00 | 7.00 | 7.00 |
| Aqueous mixture | | Water | To 100 | To 100 | To 100 |
| | Emulsification stabilizer | Salt | 1.00 | 1.00 | 1.00 |
| | Humectant | Glycerine | 8.000 | 8.000 | 8.000 |
| | | Fragrance | 0.400 | 0.400 | 0.400 |
| | Total | | 100 | 100 | 100 |

In Table 1, disteardimonium hectorite serves as a thickener, poly(methyl methacrylate) serves as an extender pigment and titanium dioxide/aluminum hydroxide/stearic acid serves as an inorganic anti-UV agent.

Examples and Comparative Example

Preparation of Urethane Foams

Polyether-based urethane foams were prepared as described in Table 2. The number of pores per inch was measured by counting and averaging the number of pores per inch of a horizontal or vertical line according to WI-QA-14 (ASTM).

TABLE 2

| | Example 1 | Example 2 | Comparative Example |
|---|---|---|---|
| Number of pores per inch (ppi) | 50 | 150 | 100 |
| Asker type F hardness | 80 | 30 | 40 |

Test Example 1

Evaluation of Stability of Urethane Foam Carrier Depending on Viscosity of Cosmetic Composition The cosmetic compositions prepared in Preparation Examples 1-3 were impregnated in the urethane foams of Examples 1-2 and Comparative Example and then stability was evaluated. Filling ability, impregnating ability and discharging ability were evaluated. The filling ability was measured as the time required to fill 15 g of the cosmetic composition. The impregnating ability was measured as the amount of the cosmetic composition impregnated in the container after impregnating 15 g of the cosmetic composition. The discharging ability was measured as the amount of the cosmetic composition ejected when the cosmetic composition impregnated in the container was applied once using a puff. The result is given in Table 3.

TABLE 3

| Cosmetic compositions | Preparation Example 1 (3,000 cps) | Preparation Example 2 (40,000 cps) |
|---|---|---|
| Example 1 50 ppi hardness 80 | Filling ability ⊚ Impregnating ability ⊚ Discharging ability ⊚ | Filling ability: Δ Impregnating ability: ○ Discharging ability: X (excessive ejection due to high viscosity and small ppi) |
| Example 2 150 ppi hardness 30 | Filling ability ○ Impregnating ability X (separation from carrier) Discharging ability ○ | Filling ability: ⊚ Impregnating ability: ⊚ Discharging ability: ⊚ |
| Comparative Example: A content with a viscosity of 8000 cps was absorbed in a foam having 100 ppi and a hardness of 40. Filling ability: Δ, impregnating ability: Δ, discharging ability: X | | |

⊚: very good,
○: good,
Δ: moderate,
X: poor.

As seen from above, the urethane foam of Example 1 whose number of pores per inch is 10-90 and Asker type F hardness is 50-100 can stably hold the cosmetic composition having a viscosity of 1,000-5,000 cps and the urethane foam of Example 2 whose number of pores per inch is 90-200 and Asker type F hardness is 1-50 can stably hold the cosmetic composition having a viscosity of 15,000-60,000 cps.

Test Example 2

Evaluation of Preference Depending on Viscosity of Cosmetic Composition

After impregnating the cosmetic compositions of Preparation Examples 1-3 in the polyether-based urethane foams of Examples 1-2 and Comparative Example, preference for the urethane foams was evaluated. Specifically, 100 women were divided into 5 groups with 20 people each. They were asked to apply the cosmetic compositions of Preparation Examples 1-2 absorbed in the polyether-based urethane foams of Examples 1-2 and Comparative Example for 2 days using a Rubycell puff and to evaluate overall preference considering feeling of use, applicability, uniformness, etc. They were asked to grade the preference with a maximum of 100 points based on pay-off (ejection) amount, application amount, convenience of use, or the like. The result is given in Table 4. An adequate pay-off amount, which can vary from user to user, leads to adequate application of the cosmetic composition, with less lumping and uniform covering.

TABLE 4

|  | impregnated cosmetic composition | Preference score |
|---|---|---|
| Example 1 | Preparation Example 1 | 50 |
| Example 2 | Preparation Example 1 | 85 |
| Comparative Example | Preparation Example 1 | 70 |
| Example 1 | Preparation Example 2 | 90 |
| Example 2 | Preparation Example 2 | 40 |
| Comparative Example | Preparation Example 2 | 70 |

As seen from above, the preference for the cosmetic composition having a viscosity of 1,000-5,000 cps was the highest when it was absorbed in the urethane foam of Example 1 which had a number of pores per inch of 10-90 and an Asker type F hardness of 50-100. And, the preference for the cosmetic composition having a viscosity of 15,000-60,000 cps was the highest when it was absorbed in the urethane foam of Example 2 which had a number of pores per inch of 90-200 and an Asker type F hardness of 1-50.

As described above, low-viscosity and high-viscosity cosmetic compositions can be stably impregnated in a urethane foam whose number of pores per inch and hardness are controlled according thereto. In addition, by selecting an adequate urethane foam depending on the viscosity of the cosmetic composition, a cosmetic which is convenient to use and carry can be prepared.

The invention claimed is:

1. A cosmetic comprising:
    a cosmetic composition of viscosity of 1,000-5,000 centipoise (cps) or 15,000-60,000 cps; and
    a urethane foam carrier, which is impregnated with the cosmetic composition,
    wherein the urethane foam has a hardness of 50 to 100 when measured with an Asker hardness tester type F before impregnation and a number of pores per inch (ppi) of greater than or equal to 10 but less than 90 when the cosmetic composition has a viscosity of 1,000-5,000 centipoise (cps), and
    wherein the urethan foam has a hardness of greater than or equal to 1 but less than 50 when measured with an Asker hardness tester type F before impregnation and a number of pores per inch (ppi) of 90 to 200 when the cosmetic composition has a viscosity of 15,000-60,000 cps.

2. The cosmetic according to claim 1, wherein the urethane foam is a polyether-based urethane foam.

3. The cosmetic according to claim 1, wherein the cosmetic composition is an aqueous dispersion, an oily dispersion, a water-in-oil (W/O) emulsion or an oil-in-water (O/W) emulsion.

4. A cosmetic comprising:
    a cosmetic composition of viscosity of 2,000 to 3,000 centipoise (cps) or 30,000 to 50,000 cps; and
    a urethane foam carrier, which is impregnated with the cosmetic composition,
    wherein the urethane foam has a hardness of 60 to 90 when measured with an Asker hardness tester type F before impregnation and a number of pores per inch (ppi) of 30 to below 70 when the cosmetic composition has a viscosity of 2,000 to 3,000 cps, and
    wherein the urethane foam has a hardness of 15 to 35 when measured with an Asker hardness tester type F before impregnation and a number of pores per inch (ppi) of 120 to 170 when the cosmetic composition has a viscosity of 30,000 to 50,000 cps.

5. The cosmetic according to claim 4, wherein the urethane foam is a polyether-based urethane foam.

6. The cosmetic according to claim 4, wherein the cosmetic composition is an aqueous dispersion, an oily dispersion, a water-in-oil (W/O) emulsion or an oil-in-water (O/W) emulsion.

* * * * *